United States Patent
Canham et al.

(10) Patent No.: US 9,243,144 B2
(45) Date of Patent: Jan. 26, 2016

(54) COMPOSITION CONTAINING LOADED AND CAPPED POROUS SILICA PARTICLES

(75) Inventors: Leigh Canham, Worcestershire (GB); Qurrat Ul Ain Shabir, Worcestershire (GB); Armando Loni, Hereford and Worcester (GB)

(73) Assignee: PSIMEDICA LIMITED, Worcestershire (GB)

( * ) Notice: Subject to any disclaimer, the term of this patent is extended or adjusted under 35 U.S.C. 154(b) by 345 days.

(21) Appl. No.: 13/121,877

(22) PCT Filed: Sep. 30, 2009

(86) PCT No.: PCT/GB2009/051278
§ 371 (c)(1),
(2), (4) Date: Jun. 2, 2011

(87) PCT Pub. No.: WO2010/038064
PCT Pub. Date: Apr. 8, 2010

(65) Prior Publication Data
US 2011/0236493 A1 Sep. 29, 2011

(30) Foreign Application Priority Data
Sep. 30, 2008 (GB) .................................. 0817936.8

(51) Int. Cl.
| | |
|---|---|
| A61K 8/11 | (2006.01) |
| A61K 8/25 | (2006.01) |
| A61K 9/14 | (2006.01) |
| A61K 9/50 | (2006.01) |
| A23L 1/00 | (2006.01) |
| C09C 1/28 | (2006.01) |
| A23L 1/22 | (2006.01) |
| A61K 8/34 | (2006.01) |
| A61K 8/73 | (2006.01) |
| A61Q 5/02 | (2006.01) |
| A61Q 11/00 | (2006.01) |
| A61Q 19/00 | (2006.01) |
| C09C 1/30 | (2006.01) |

(52) U.S. Cl.
CPC ............... *C09C 1/28* (2013.01); *A23L 1/0029* (2013.01); *A23L 1/22016* (2013.01); *A23L 1/22041* (2013.01); *A61K 8/11* (2013.01); *A61K 8/25* (2013.01); *A61K 8/347* (2013.01); *A61K 8/733* (2013.01); *A61K 8/736* (2013.01); *A61Q 5/02* (2013.01); *A61Q 11/00* (2013.01); *A61Q 19/00* (2013.01); *C09C 1/30* (2013.01); *A61K 2800/412* (2013.01); *C01P 2006/14* (2013.01); *C01P 2006/16* (2013.01)

(58) Field of Classification Search
None
See application file for complete search history.

(56) References Cited

U.S. PATENT DOCUMENTS

| | | | |
|---|---|---|---|
| 4,568,559 | A * | 2/1986 | Nuwayser et al. ............ 427/2.15 |
| 7,939,103 | B2 | 5/2011 | Dahne et al. |
| 2005/0031699 | A1 * | 2/2005 | Simonnet et al. ............. 424/489 |
| 2006/0073205 | A1 * | 4/2006 | Ohta et al. .................... 424/471 |
| 2006/0154069 | A1 * | 7/2006 | Lin et al. ....................... 428/402 |
| 2009/0175985 | A1 | 7/2009 | Canham |

FOREIGN PATENT DOCUMENTS

| | | | | |
|---|---|---|---|---|
| EP | 0 816 484 | A2 | 1/1998 | |
| EP | 0 930 334 | A1 | 7/1999 | |
| EP | 1 795 075 | | 6/2007 | |
| EP | 1795075 | A1 * | 6/2007 | ............... A23L 1/22 |
| JP | 61-155307 | | 7/1986 | |
| JP | 64-1799 | | 1/1989 | |
| JP | 7-173452 | | 7/1995 | |
| JP | 8-500144 | | 1/1996 | |
| JP | 10-60482 | | 3/1998 | |
| JP | 2001-520983 | | 11/2001 | |
| JP | 2003-505537 | | 2/2003 | |
| JP | 2005-47893 | | 2/2005 | |
| JP | 2007-529303 | | 10/2007 | |
| JP | 2009-012996 | | 1/2009 | |
| WO | WO 94/04267 | | 3/1994 | |
| WO | WO 99/21532 | | 5/1999 | |
| WO | WO 01/05926 | A1 | 1/2001 | |
| WO | WO 2005/009602 | | 2/2005 | |
| WO | WO 2007012847 | A1 * | 2/2007 | ............... A23L 1/22 |
| WO | WO 2007/031345 | | 3/2007 | |

OTHER PUBLICATIONS

Ohta et al, "Development of a Simple Method for the preparation of a Silica Gel Based Controlled Delivery System with a High Drug Content", European Journal of Pharmaceutical Sciences, vol. 26, 2005, pp. 87-96, XP002562365.

International Preliminary Report on Patentability in PCT/GB2009/051278 dated Apr. 14, 2011.

International Search Report for PCT/GB2009/051278, mailed Feb. 4, 2010.

Written Opinion of the International Searching Authority for PCT/GB2009/051278, mailed Feb. 4, 2010.

UK Search Report for GB0817936.8, dated Jan. 27, 2009.

Ohta, K.M. et al., "Development of a Simple Method for the Preparation of a Silica Gel Based Controlled Delivery System with a High Drug Content", European Journal of Pharmaceutical Sciences, vol. 26, (2005), pp. 87-96.

* cited by examiner

*Primary Examiner* — Michael B Pallay
(74) *Attorney, Agent, or Firm* — Nixon & Vanderhye P.C.

(57) ABSTRACT

A consumer care composition or a food composition comprising a mesoporous microparticulate material wherein at least some of the pores of the material are loaded with at least one ingredient and the loaded mesoporous microparticulate material is encapsulated by a capping layer is described.

6 Claims, No Drawings

COMPOSITION CONTAINING LOADED AND CAPPED POROUS SILICA PARTICLES

This application is the U.S. national phase of International Application No. PCT/GB2009/051278 filed 30 Sep. 2009, which designated the U.S. and claims priority to GB Application No. 0817936.8 filed 30 Sep. 2008, the entire contents of each of which are hereby incorporated by reference.

FIELD OF THE INVENTION

This invention relates to compositions comprising loaded microencapsulated materials, methods for producing said compositions and uses of said microencapsulated materials and compositions.

BACKGROUND OF THE INVENTION

In the consumer care and food industries, various methods are used to stabilise various ingredients and to control the timing and release of said ingredients. Such methods enable the protection of food components to ensure against nutritional loss and to mask or preserve flavours and aromas. Suitable methods of protection also increase the stability of vitamin or mineral supplements which are normally sensitive to light, UV radiation, metals, humidity, temperature and oxygen. Similar issues affect a range of consumer care products such as hair care compositions, oral hygiene compositions, skin care products and cosmetics.

There is a continued need for alternative methods and/or products for protecting, controlling the release of, and/or masking the taste of ingredients in the consumer care and food industries. In particular, there are challenges in storing products in liquid environments.

SUMMARY OF THE INVENTION

The present invention provides for the use of an encapsulated mesoporous microparticulate material comprising at least one loaded ingredient in a composition, such as a consumer care or food composition. More specifically, and according to a first aspect of the present invention, there is provided a consumer care composition or a food composition comprising a mesoporous microparticulate material wherein at least some of the pores of the material are loaded with at least one ingredient and the mesoporous microparticulate material is encapsulated by a capping layer.

According to a second aspect of the present invention, there is provided a production process for said consumer care or food composition according to the first aspect of the present invention, comprising blending said mesoporous microparticulate material and other components of the consumer care or food composition.

According to a further aspect of the present invention, a method is provided of treating and/or cleaning the human body and/or face comprising applying a composition according to the first aspect of the present invention to the human face and/or body wherein the composition is a cosmetic composition. For example, methods of treating and/or preventing any one of acne, oily skin, wrinkles, psoriasis on the body and/or face are provided. The method may be a non-medical (i.e. "cosmetic") or medical treatment method. The present invention extends to said compositions for use in the prevention and/or treatment of one or more of acne, oily skin, wrinkles, psoriasis, skin blemishes such as birthmarks, scars, moles, blackheads, freckles, pimples, bags or dark circles under the eyes, rosacea, sebhorrhoeic dermatitis, enlarged pores, pitting, enlarged blood vessels, senile freckles on the body and/or face.

According to a further aspect of the present invention a method of treating and/or cleaning the hair and/or scalp of a human or animal comprising applying a composition according to the first aspect of the present invention is provided wherein the composition is a hair care composition. The method may be a cosmetic method. The hair care composition may be an anti-dandruff shampoo and/or suitable for treating split ends. The present invention extends to said hair care compositions for use in the prevention and/or treatment of dandruff and/or split ends and/or head-lice and/or hair-loss.

According to a further aspect of the present invention, a method for reducing stain and/or plaque and/or gingivitis comprising the application of a safe and effective amount of a composition according to the first aspect of the invention to the teeth and other oral surfaces is provided wherein the composition is an oral hygiene composition.

According to a further aspect of the present invention, the use of a composition according to the first aspect of the invention in the manufacture of a medicinal oral hygiene composition, such as a dentifrice composition, for reducing plaque and/or for reducing or inhibiting gingivitis is provided wherein the composition is an oral hygiene composition.

According to a further aspect of the present invention, a cosmetic method for reducing stain comprising the application of a safe and effective amount of a composition according to the first aspect of the invention to the teeth and other oral surfaces is provided wherein the composition is an oral hygiene composition.

According to a further aspect of the present invention, a composition according to the first aspect of the invention for use in the treatment and/or the prevention of plaque and/or gingivitis is provided wherein the composition is an oral hygiene composition.

According to a further aspect of the present invention, there is provided the use of a mesoporous microparticulate material, wherein at least some of the pores of the material are loaded with at least one ingredient and the mesoporous microparticulate material is encapsulated by a capping layer, in a food composition, wherein the ingredient is a food ingredient, for improving the bioavailability of said food ingredient and wherein the food ingredient is released on contact with gastrointestinal fluid in the human gastrointestinal tract following ingestion.

The improvement of the bioavailability of the food ingredient may be at least 50% when compared to the at least one ingredient in the absence of the mesoporous microparticulate material.

According to a further aspect of the present invention, there is provided the use of a mesoporous microparticulate material in a hair care composition wherein at least some of the pores of the material are loaded with at least one ingredient and the mesoporous microparticulate material is encapsulated by a capping layer wherein the ingredient is a hair care active, for improving the retention of said hair care active ingredient on the hair and/or scalp and/or improving the dissolution of the active on application to the hair.

The improvement in retention may be at least 50% when compared to the at least one ingredient in the absence of the mesoporous microparticulate material and the improvement in dissolution may be at least 500%.

Through use of the encapsulated mesoporous microparticulate material the compositions according to the present invention seek to provide at least one of the following: high bioavailability of loaded ingredients (including active materials) through combined nanoentrapment and microencapsulation; high loading capacity plus the ability to control and/or target the release of ingredients through, for example, modification of the surface chemistry. These properties and attributes are also demonstrated in liquid environments which is considered to be particularly advantageous.

Use of the encapsulated mesoporous microparticulate material according to the present invention provides for improved retention of one or more loaded active ingredients when compared to uncapped versions of the material. For example, less than about 25 wt % of the active may be lost during storage, preferably less than 10 wt %, more preferably less than 5 wt %. The length of storage may typically vary from 1 year to 5 years. Following the opening of the container in which the composition is stored, the length of storage may be, for example, up to 1 year or 2 years.

DETAILED DESCRIPTION OF THE INVENTION

Mesoporous Microparticulate Material

Suitable mesoporous materials include organic and inorganic materials. More specifically, suitable mesoporous materials include mesoporous silicon, mesoporous silica, mesoporous silicate, mesoporous starch, mesoporous carbon, mesoporous alumina, mesoporous titania, mesoporous carbonate.

Mesoporous materials contain pores having a diameter in the range of 2 to 50 nm and microparticles are particles of about 1 to 1000 μm in diameter.

In the present invention, particle size distribution measurements, including the mean particle size ($d_{50}$/μm) of the particles are measured using a Malvern Particle Size Analyzer, Model Mastersizer, from Malvern Instruments. A helium-neon gas laser beam is projected through a transparent cell which contains the silicon particles suspended in an aqueous solution. Light rays which strike the particles are scattered through angles which are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the silicon.

The average pore diameter is measured using a known technique. Mesopore diameters are measured by very high resolution electron microscopy. This technique and other suitable techniques which include gas-adsorption-desorption analysis, small angle x-ray scattering, NMR spectroscopy or thermoporometry, are described by R. Herino in "Properties of Porous Silicon", chapter 2.2, 1997.

The mesoporous material may have a BET surface area of 10 $m^2$/g to 700 $m^2$/g for example 100 $m^2$/g to 400 $m^2$/g. The BET surface area is determined by a BET nitrogen adsorption method as described in Brunauer et al., J. Am. Chem. Soc., 60, p 309, 1938. The BET measurement is performed using an Accelerated Surface Area and Porosimetry Analyser (ASAP 2400) available from Micromeritics Instrument Corporation, Norcross, Ga. 30093. The sample is outgassed under vacuum at 350° C. for a minimum of 2 hours before measurement.

The surface area and the size of the pores in the material may to some extent depend on what application the mesoporous material is to be used for. For example, the BET surface area of the mesoporous material is preferably in excess of 0.1 $m^2$/g for microorganism entrapment, and preferably greater than 100 $m^2$/g for biodegradability in intestinal fluid.

Methods for making microparticles are well known in the art. These include chemical or gas phase synthesis methods or electrochemical etching or comminution (e.g. milling as described in Kerkar et al. J. Am. Ceram. Soc., vol. 73, pages 2879-2885, 1990).

As used herein, and unless otherwise stated, the term "silicon" refers to solid elemental silicon. For the avoidance of doubt, and unless otherwise stated, it does not include silicon-containing chemical compounds such as silica, silicates or silicones, although it may be used in combination with these materials.

The purity of the silicon may depend to some extent on the final application of the mesoporous silicon. For example, the silicon may be about 95 to 99.99999% pure, for example about 96 to 99.9% pure. So-called metallurgical silicon which is suitable for use in a range of applications, including foodstuffs, has a purity of about 98 to 99.5%. In connection with cosmetic formulations, the metallurgical grade silicon preferably has a very low content of all metals (e.g. nickel) known to cause problems in connection with skin hypersensitivity. Also, with regard to hair compositions, any particular metals which may cause scalp irritation may be minimised, these include nickel, copper and silver. For example, any nickel which may be present preferably does not exceed 100 ppm.

The physical forms of silicon which are suitable for use according to the present invention may be chosen from or comprise one or more of amorphous silicon, single crystal silicon and polycrystalline silicon (including nanocrystalline silicon, the grain size of which is typically taken to be 1 to 100 nm) and including combinations thereof. Any of the above-mentioned types of silicon may be porosified to form mesoporous silicon.

Methods for making silicon powders such as silicon microparticles are well known in the art. Methods for making silicon powders are often referred to as "bottom-up" methods, which include, for example, chemical synthesis or gas phase synthesis. Alternatively, so-called "top-down" methods refer to such known methods as electrochemical etching or comminution (e.g. milling as described in Kerkar et al. J. Am. Ceram. Soc., vol. 73, pages 2879-2885, 1990). PCT/GB02/03493 and PCT/GB01/03633, the contents of which are incorporated herein by reference in their entirety, describe methods for making particles of silicon, said methods being suitable for making silicon for use in the present invention. Such methods include subjecting silicon to centrifuge methods, or grinding methods.

The mesoporous silicon for use in the present invention may be derivatised. Derivatised porous silicon is porous silicon possessing a covalently bound monolayer on at least part of its surface. The monolayer typically comprises one or more organic groups that are bonded by hydrosilylation to at least part of the surface of the porous silicon. Derivatised porous silicon is described in PCT/GB00/01450, the contents of which are incorporated herein by reference in their entirety. PCT/GB00/01450 describes derivatisation of the surface of silicon using methods such as hydrosilyation in the presence of a Lewis acid. In that case, the derivatisation is effected in order to block oxidation of the silicon atoms at the surface and so stabilise the silicon. Methods of preparing derivatised porous silicon are known to the skilled person and are described, for example, by J. H. Song and M. J. Sailor in Inorg. Chem. 1999, vol 21, No. 1-3, pp 69-84 (Chemical Modification of Crystalline Porous Silicon Surfaces). Derivitisation of the silicon may be desirable when it is required to increase the hydrophobicity of the silicon, thereby decreasing its wettability. Preferred derivatised surfaces are modified with one or more alkyne groups. Alkyne derivatised silicon may be derived from treatment with acetylene gas, for example, as described in "Studies of thermally carbonized porous silicon surfaces" by J. Salonen et al in Phys Stat. Solidi (a), 182, pp 123-126, (2000) and "Stabilisation of porous silicon surface by low temperature photoassisted reaction with acetylene", by S. T. Lakshmikumar et al in Curr. Appl. Phys. 3, pp 185-189 (2003). The mesoporous silicon may be derivatised during its formation in HF-based electrolytes, using the techniques described by G. Mattei and V. Valentini in Journal American Chemical Society vol 125, p 9608 (2003) and Valentini et al., Physica Status Solidi (c) 4 (6) p 2044-2048 (2007).

Methods for making various forms of silicon which are suitable for use in the present invention are described below. The methods described are well known in the art.

In PCT/GB96/01863, the contents of which are incorporated herein by reference in their entirety, it is described how bulk crystalline silicon can be rendered porous by partial electrochemical dissolution in hydrofluoric acid based solutions. This etching process generates a silicon structure that retains the crystallinity and the crystallographic orientation of the original bulk material. Hence, the porous silicon formed is a form of crystalline silicon. Broadly, the method involves anodising, for example, a heavily boron doped CZ silicon wafer in an electrochemical cell which contains an electrolyte comprising a 20% solution of hydrofluoric acid in an alcohol such as ethanol, methanol or isopropylalcohol (IPA). Following the passing of an anodisation current with a density of about 50 mAcm$^{-2}$, a porous silicon layer is produced which may be separated from the wafer by increasing the current density for a short period of time. The effect of this is to dissolve the silicon at the interface between the porous and bulk crystalline regions. Porous silicon may also be made using the so-called stain-etching technique which is another conventional method for making porous silicon. This method involves the immersion of a silicon sample in a hydrofluoric acid solution containing a strong oxidising agent. No electrical contact is made with the silicon, and no potential is applied. The hydrofluoric acid etches the surface of the silicon to create pores.

The mesoporous silicon may be generated from a variety of non-porous silicon powders by so-called "electroless electrochemical etching techniques", as reviewed by K. Kolasinski in Current Opinions in Solid State & Materials Science 9, 73 (2005). These techniques include "stain-etching", "galvanic etching", "hydrothermal etching" and "chemical vapour etching" techniques. Stain etching results from a solution containing fluoride and an oxidant. In galvanic or metal-assisted etching, metal particles such as platinum are also involved. In hydrothermal etching, the temperature and pressure of the etching solution are raised in closed vessels. In chemical vapour etching, the vapour of such solutions, rather than the solution itself is in contact with the silicon. Mesoporous silicon can be made by techniques that do not involve etching with hydrofluoric acid. An example of such a technique is chemical reduction of various forms of porous silica as described by Z. Bao et al in Nature vol. 446 8 Mar. 2007 p 172-175 and by E. Richman et al. in Nano Letters vol. 8(9) p 3075-3079 (2008). If this reduction process does not proceed to completion then the mesoporous silicon contains varying residual amounts of silica.

Following its formation, the mesoporous silicon may be dried. For example, it may be supercritically dried as described by Canham in Nature, vol. 368, (1994), pp 133-135. Alternatively, the mesoporous silicon may be freeze dried or air dried using liquids of lower surface tension than water, such as ethanol or pentane, as described by Bellet and Canham in Adv. Mater, 10, pp 487-490, 1998.

Silicon hydride surfaces may, for example, be generated by stain etch or anodisation methods using hydrofluoric acid based solutions. When the silicon is prepared, for example, by electrochemical etching in HF based solutions, the surface of the mesoporous silicon may or may not be suitably modified in order, for example, to improve the stability of the mesoporous silicon in the composition. In particular, the surface of the mesoporous silicon may be modified to render the silicon more stable in alkaline conditions. The surface of the mesoporous silicon may include the external and/or internal surfaces formed by the pores of the mesoporous silicon.

In certain circumstances, the stain etching technique may result in partial oxidation of the mesoporous silicon surface. The surfaces of the mesoporous silicon may therefore be modified to provide: silicon hydride surfaces; silicon oxide surfaces wherein the mesoporous silicon may typically be described as being partially oxidised; or derivatised surfaces which may possess Si—O—C bonds and/or Si—C bonds. Silicon hydride surfaces may be produced by exposing the mesoporous silicon to HF.

Silicon oxide surfaces may be produced by subjecting the silicon to chemical oxidation, photochemical oxidation or thermal oxidation, as described for example in Chapter 5.3 of Properties of Porous Silicon (edited by L. T. Canham, IEE 1997). PCT/GB02/03731, the entire contents of which are incorporated herein by reference, describes how mesoporous silicon may be partially oxidised in such a manner that the sample of mesoporous silicon retains some elemental silicon. For example, PCT/GB02/03731 describes how, following anodisation in 20% ethanoic HF, the anodised sample was partially oxidised by thermal treatment in air at 500° C. to yield a partially oxidised mesoporous silicon sample.

The surface of the elemental mesoporous silicon may comprise one or more silicon compounds. For example, at least some of the mesoporous silicon surface may comprise silicon bonded to oxygen to form an oxide layer. The silicon particles may possess an oxide content corresponding to between about one monolayer of oxygen and a total oxide thickness of less than or equal to about 4.5 nm covering the entire silicon skeleton. The mesoporous silicon may have an oxygen to silicon atomic ratio between about 0.04 and 2.0, and preferably between 0.60 and 1.5. Oxidation may occur in the pores and/or on the external surface of the silicon.

Suitable other mesoporous materials include: mesoporous silicates (or bioactive glasses) as described in J. Controlled Release 110, 522(2006); mesoporous carbonates as described in U.S. Pat. No. 6,749,825; mesoporous silica gels as described in European J. Pharma. Sciences 26, 87 (2005) and Materials Lett. 19, 217 (1994); mesoporous starch derivatives as described in Green Chemistry 9,992 (2007); mesoporous alumina as described in Chem. Commun. 1986-1987 (2005); mesoporous carbon materials as reviewed in Angewandte Chemie 7, (20) 3696 (2008); mesoporous titania as described in Mater. Lett 59, 3308 (2005). The contents of these references are incorporated herein in their entirety by reference.

The Loaded Ingredient

The microparticulate material is loaded such that one or more ingredients are present in the pores of the material. The loaded ingredient or ingredients may be referred to as being entrapped.

Generally the loaded one or more ingredients may be selected from one or more of the following: food ingredients (including those that are hydrophobic or degraded by the acidic conditions of the human or animal stomach), nutrients, hair care ingredients (including those that are light sensitive and/or whose efficacy benefits from improved retention on the scalp and/or hair follicles), cosmetic ingredients (including those that require segregation from other ingredients in the formulation), oral care ingredients (including those whose efficacy benefits from improved retention in the oral cavity).

The ingredient to be loaded with the mesoporous material may be dissolved or suspended in a suitable solvent, and mesoporous particles may be incubated in the resulting solution for a suitable period of time. Both aqueous and non-aqueous slips have been produced from ground silicon powder and the processing and properties of silicon suspensions have been studied and reported by Sacks in Ceram. Eng. Sci. Proc., 6, 1985, pp 1109-1123 and Kerkar in J. Am. Chem. Soc. 73, 1990, pp 2879-85. The removal of solvent will result in the ingredient penetrating into the pores of the mesoporous material by capillary action, and, following solvent removal, the ingredient will be present in the pores. Preferred solvents, at least for use in connection with mesoporous silicon, are water, ethanol, and isopropyl alcohol, GRAS solvents and volatile liquids amenable to freeze drying.

Typically, the one or more ingredients are present in the range, in relation to the loaded mesoporous microparticulate material, of 0.01 to 90 wt %, for example 1 to 40 wt %, for example 20 to 50 wt % (optionally, in combination with about 70% porosity) and for example 2 to 10 wt %.

Higher levels of loading, for example, at least about 15 wt % of the loaded ingredient based on the loaded weight of the mesoporous material may be achieved by performing the impregnation at an elevated temperature. For example, loading may be carried out at a temperature which is at or above the melting point of the ingredient to be loaded. Quantification of gross loading may conveniently be achieved by a number of known analytical methods, including gravimetric, EDX (energy-dispersive analysis by x-rays), Fourier transform infra-red (FTIR), Raman spectroscopy, UV spectrophotometry, titrimetric analysis, HPLC or mass spectrometry. If required, quantification of the uniformity of loading may be achieved by techniques that are capable of spatial resolution such as cross-sectional EDX, Auger depth profiling, micro-Raman and micro-FTIR.

The loading levels can be determined by dividing the volume of the ingredient taken up during loading (equivalent to the mass of the ingredient taken up divided by its density) by the void volume of the mesoporous material (e.g. silicon) prior to loading multiplied by one hundred.

The Capping Layer

The capping layer serves to encapsulate the mesoporous microparticulate material. In encapsulating the mesoporous material, the openings to the pores are sealed. Typically, the whole of the particle, or substantially all of the particle, is coated with the capping layer and the capping layer may be referred to herein as a bead. The capping layer at least seals the openings to the pores at the surface of the mesoporous material, thus ensuring that the at least one loaded ingredient is retained. The capping layer, or bead, may encapsulate more than a single mesoporous microparticulate material. The thickness of the capping layer may be about 0.1 to 50 μm in thickness, for example about 1 to 10 μm, for example about 1 to 5 μm. The capping layer may provide retention of an ingredient over a period of a few months to many months, for example up to about 5 years, followed by triggered release through site specific degradation which may occur in or on the human or animal body. The capping layer may be an organic or an inorganic capping layer. The encapsulated particles may consist essentially of inorganic particles capped with an organic material or an organic particle capped with an inorganic material. Alternatively, the encapsulated particles may consist essentially of organic particles capped with an organic material or inorganic particles capped with an inorganic material.

The thickness of the capping layer is measured by mechanically fracturing a number of the capped particles and examining their cross-sectional images in a high resolution scanning electron microscope, equipped with energy dispersive x-ray analysis (EDX analysis) of chemical composition. Alternatively, if the particle size distributions are measured accurately, before and after capping, then the average thickness of micron thick layer caps can be estimated. For relatively narrow particle size distributions and uniform coatings, if the density of the capping layer is known accurately, then accurate gravimetric measurements of weight increase that accompanies capping can also yield an average cap thickness.

Advantageously, the capping layer may comprise, consist of, or consist essentially of, a material which is present in the loaded ingredient. For example, when the loaded mesoporous material is for use in dentifrice compositions, such as toothpaste, then the capping layer may include one or more of: titanium dioxide, carageenan, xanthum gum, cellulose gum, tocopherol. Similarly, when the loaded mesoporous material is intended for use in chocolate then the capping layer may include one or more of: cocoa butter, vegetable fat, milk fat, lecithin. As a further illustration, when the loaded mesoporous material is intended for use in shampoo, then the capping layer may include one or more of glyceryl oleate, seed oil, cyclopentasiloxane, paraffin. Preferably, the capping layer has GRAS status for food and nutritional formulations. The functions of capping layer and loaded ingredient may be provided by the same material.

The capping layer may comprise one or more than one distinct layer. For example, the capping layer may comprise a hydrophilic layer and a hydrophobic layer. Where there are distinct layers present of different materials then one of the layers may overlie the other.

The capping layer or layers may be selected from one or more of the following, which are of particular use in connection with consumer care formulations: carbohydrates, gums, lipids, proteins, celluloses, polymers, elastomers, inorganic materials.

Suitable examples of carbohydrates include starch, dextran, sucrose, corn, syrup. Suitable examples of gums include carrageenan, alginate, e.g. sodium alginate, gum Arabic, chitosan, agar. Suitable examples of lipids include fats, hardened oils, paraffin, stearic acid, wax, diglycerides, monoglycerides. Suitable examples of proteins include albumin, casein, gluten, gelatine. Suitable examples of celluloses include carbomethylcellulose, acetylcellulose, methylcellulose. Suitable examples of polymers include synthetic polymers such as polyacrylate, polyethylene, polystyrene, polyvinyl alcohol, polyurea. Suitable examples of elastomers include acrylonitrile, polybutadience. Suitable examples of inorganic materials include calcium sulphate, silicates, clays, silicon, silicon dioxide, calcium phosphate. The capping layer may comprise, consist of, or consist essentially of elemental silicon, for example, in the form of an amorphous silicon coating or a discontinuous layer of silicon nanoparticles.

Suitable methods for capping the mesoporous material include: spray drying, fluidised bed coating, pan coating, modified microemulsion techniques, melt extrusion, spray chilling, complex coacervation, vapour deposition, solution precipitation, emulsification, supercritical fluid techniques, physical sputtering, laser ablation, very low temperature sintering and thermal evaporation.

Spray drying techniques, especially in the food industry, are usually carried out from aqueous feed formulations, in which case the capping layer should be soluble in water at an acceptable level. Typical materials include gum acacia, maltodextrins, hydrophobically modified starch and mixtures thereof. Other polysaccharides such as alginate, carboxymethylcellulose, guar gum and proteins such as whey proteins, soy proteins, sodium caseinate are also suitable. Aqueous two phase systems (ATPs) which may result from the phase separation of a mixture of soluble polymers in a common solvent due to the low entropy of mixing of polymer mixtures can be used to design double encapsulated ingredients in a single spray drying step.

Spray chilling or cooling is generally considered one of the least expensive encapsulation technologies. This technique may also be referred to as matrix encapsulation. It is particularly suitable for encapsulating organic and inorganic materials as well as textural ingredients, enzymes, flavours and other ingredients to improve heat stability. Matrix encapsulation may lead to some of the loaded ingredient being incorporated in the capping layer.

Extrusion is suitable for the encapsulation of volatile and unstable flavours. This process is suitable for imparting long shelf life to normally oxidation prone flavour compounds such as citrus oils.

Coacervation is particularly useful in connection with the use of high levels of loaded ingredient and is typically used for encapsulating flavour oils, fish oils, nutrients, vitamins, preservatives, enzymes. Coacervation requires the phase separation of one or many hydrocolloids from solution and the subsequent deposition of the newly formed coacervate phase around the mesoporous material which is suspended or emulsified in the same reaction media. The hydrocolloid shell may then be crosslinked using an appropriate chemical or enzymatic crosslinker if required.

When the capping layer includes elemental silicon, the amorphous silicon coating may be deposited by physical sputtering and may have a thickness of 500 nm to 5 µm. The silicon nanoparticles are preferably bound to the silicon microparticles by solution based techniques. The silicon nanoparticles typically possess a particle size distribution comparable to that of the mesopore particle size distribution of the microparticles.

There are various mechanisms by which the release of the loaded ingredient may be triggered. These are set out in (a) to (f) below.

(a) Biodegradation

The capping layer may be degraded by enzymes or bacteria present at the intended site of use (active release). An example is starch degraded by salivary amylase for oral hygiene products.

(b) Mechanical

The capping layer may be degraded by mechanical forces at the intended site of use, such as frictional forces upon application of cosmetics, or more severe forces exerted when, brushing teeth or biting food.

(c) Thermal

The capping layer may be degraded by a sudden increase of temperature such as exposure to body temperature (37° C.) or freshly boiled water (70-90° C.) in the case of hot drinks or the application of a hair dryer.

(d) Optical Irradiation

The capping layer may be degraded by exposure to sunlight or UV from commercial tanning equipment.

(e) Microwave Irradiation

The capping layer may be degraded by the radiation from commercial microwave ovens.

(f) Chemical Environment

The capping layer may be degraded by a change in the chemical environment, such as a pH change from acidic to alkali or vice versa. In particular, the changes may be those associated with ingestion, and where the pH and composition of intestinal fluid promotes degradation.

Compositions

The loaded microencapsulated materials are suitable for use in a range of compositions including consumer care compositions and food compositions. The consumer care compositions include hair care compositions, oral hygiene compositions, cosmetic compositions. Preferably, the use of pharmaceutical compositions is not included.

(1) Food

For use in food compositions, the loaded ingredients may be selected from one or more of: oxygen sensitive edible oils; minerals; oxygen sensitive fats including dairy fats; oil soluble ingredients; vitamins; fragrances or aromas; flavours; enzymes; probiotic bacteria; prebiotics; nutraceuticals; amino acids; herbal extracts; herbs; plant extracts; edible acids; salt; antioxidants; therapeutic agents. Typically, the one or more ingredients are present in the range, in relation to the loaded material, of 0.01 to 90 wt %, for example 1 to 40 wt %, for example 20 to 50 wt % (optionally in combination with about 70% porosity) and for example 2 to 10 wt %.

Suitable mesoporous microparticulate materials for use in food include silicon, starch, silica, mesoporous forms of GRAS ingredients.

The food may be in the form of a beverage or non-beverage. Suitable foods for use in the present invention may comprise one or more of the following: meat; poultry; fish; vegetables; fruit; chocolate and confectionary; cereals and baked products including bread, cakes, biscuits, nutrition or cereal bars; pastry; pasta; dairy products such as milk, cream, butter, margarine, eggs, ice cream, cheese. The food may be in the form of any of the following: convenience meals; frozen food; chilled food; dried food; freeze dried food; rehydrated food; pickles; soups; dips; sauces.

Suitable beverages include alcoholic and non-alcoholic beverages. Particular examples of suitable drinks include water, for example bottled water; tea; coffee; cocoa; drinking chocolate; fruit juices and smoothies; wine; beer; ales; lager; spirits. The beverages may for example be in the form of granules, including those which have been freeze dried, which are suitable for making instant coffee and tea and the like. As such, the present invention extends to products suitable for making beverages, such as instant beverage powders and granules. These include coffee granules, coffee powder, coffee tablets, tea, cocoa powder, chocolate powder. Other suitable products include coffee oil and concentrates, for example, fruit juice concentrates.

The pH of the food is preferably such that the mesoporous material does not dissolve in the food over a significant period of time and will thus afford an acceptable shelf-life. For example, for mesoporous silicon, the pH of the food is typically 2 to 6.

Oxygen Sensitive Edible Oils

Oxygen sensitive edible oils include polyunsaturated fatty acids which themselves include canola oil, borage oil, evening primrose oil, safflower oil, sunflower oil, pumpkinseed oil, rosemary oil, rice bran oil, flaxseed oil, wheatgerm oil, grapeseed oil, linseed oil. Some of these oils contribute linoleic acid, alpha-linoleic acid, oleic acid, palmitic acid, stearic acid. Also included are marine oils, for example, those derived from fish such as tuna, herring, mackerel, sardine, cod liver and shark.

Minerals and Trace Elements

Suitable minerals include: macrominerals comprising Ca, P, Mg, Na, K; microminerals comprising Fe, Zn, Cu, Se, Cr, I, Mn, Mo, F. Suitable trace elements include Ni, V, B, Co.

The blending and compression of particular metal powders with silicon powder may be used to create edible microbatteries. Following ingestion, the gastro-intestinal fluid acts as an electrolyte. If the metal is less noble than silicon then the resulting galvanic coupling increases the dissolution of that metal resulting in increased bioavailability.

Vitamins

Suitable vitamins include Ascorbic Acid, Beta-carotene, Biotin, Choline, Folic Acid, Niacin, Pantothenic Acid (Vitamin B5), Phylloquinone (Vitamin K), Pyridoxine (Vitamin B6), Riboflavin (Vitamin B2), Thiamin (Vitamin B1), Vitamin A, Vitamin B12, Vitamin D, Vitamin E and mixtures thereof. The vitamin and silicon may be combined by allowing the vitamin to impregnate the silicon, optionally in the presence of gentle heat, typically in the range of 40° C. and 200° C.

Fragrances, Aromas and Flavours

Suitable fragrances, aromas and flavours are non-toxic and suitable for foodstuffs and will be readily apparent to the skilled person, see Bauer et al, "Common Fragrances & Flavours", Wiley, 1997, pp 278. Preferred fragrances, aromas and flavours are "Generally Recognised As Safe" (GRAS) by the FDA. Alcohols, aldehydes, ketones, esters and lactones are classes of compounds most frequently used in natural and artificial fragrances.

More specifically, suitable flavours (or flavouring agents) include: one or more of spice oleoresins derived from allspice, basil, capsicum, cinnamon, cloves, cumin, dill, garlic, marjoram, nutmeg, paprika, black pepper, rosemary and tumeric; essential oils such as anise oil, caraway oil, clove oil, eucalyptus oil, fennel oil, garlic oil, ginger oil, peppermint oil, onion oil, pepper oil, rosemary oil, spearmint oil; citrus oils including orange oil, lemon oil, bitter orange oil and tangerine oil; alliaceous flavours which include garlic, leek, chive, and onion; botanical extracts such as arnica flower extract, chamomile flower extract, hops extract, and marigold extract; botanical flavour extracts such as blackberry, chicory root, cocoa, coffee, kola, liquorice root, rose hips, sarsaparilla root, sassafras bark, tamarind and vanilla extracts; protein hydrolysates such as hydrolyzed vegetable protein (HVP's), meat protein hydrolyzates, milk protein hydrolyzates; natural and artificial compounded flavours which include those disclosed in S. Heath, Source Book of Flavours, Avi Publishing Co., Westport, Conn., 1981, pp. 149-277. Particular flavour compounds are, for example: benzaldehyde, diacetyl(2,3-butanedione), vanillin, ethyl vanillin and citral (3,7-dimethyl-2,6-octadienal). The flavouring agent may be in the form of an oil, aqueous solution, non-aqueous solution or an emulsion. Flavour essences, i.e. the water soluble fraction derived from fruit or citrus can be utilized, and typically at lower levels than the ingredients mentioned above.

With regard to fragrant oils, sustained release may be carried out using mesoporous silicon possessing a pore diameter in the range of about 2-10 nm. The small pore size suppresses the release of the fragrant volatiles.

Particularly suitable food aromas (or aromatising agents) include food aromas for liquid food products, particularly instant soups and beverages such as coffee. Other suitable food aromas include those used in desserts such as instant puddings, and frozen food products such as frozen pizza. The food aromas may also be those suitable for use in food which needs to be reconstituted with hot water or milk or heated by the consumer prior to consumption. Suitable food aromas include the following: cheese aroma; aromas for hot soluble coffee-based beverages such as coffee, hazelnut, amaretto, chocolate, cream and vanilla; aromas for hot soluble tea-based beverages such as raspberry, cream and vanilla; aromas for hot cocoa-based beverages such as raspberry, amaretto, cream, chocolate and vanilla; aromas for hot soups such as mushroom, tomato, beef and chicken; aromas for beverages such as coffee, tea, cherry, grape, and strawberry; aromas for dessert products such as raspberry, chocolate, butterscotch, cherry, grape, strawberry, banana, and vanilla; aromas for other products such as cream, seafood, meat, garlic and onion. The aroma flavour may be part of an aromatizing composition which may optionally also include one or more other constituents such as a non-volatile edible fat or oil, a surfactant, a wetting agent, a foaming agent, an extremely volatile solvent, a propellant, dissolved edible solids, an antioxidant, or an aroma precursor. The total amount of such additional constituents will preferably not usually be more than about 40% by weight, based on the total weight of the mesoporous material and aroma constituents. Suitable non-volatile edible fats or oils include coffee oil or triglyceride oils used as a source of flavour or as a flavour solvent. A surfactant may also be present which acts as a spreading agent or emulsifier to control the droplet size of the aromatizing composition and its degree of spreading on the surface of a food product. Suitable highly volatile solvents such as acetone and acetaldehyde may be used as a co-solvent for the volatile food aroma and modify the rate of evaporation of the aroma delivery system. A dissolved or entrapped propellant gas such as air, nitrogen, carbon dioxide, nitrous oxide, or a gas generator such as a chemical carbonation reagent, may be included to increase buoyancy or to accelerate aroma release and evaporation. Dissolved edible solids increase the viscosity of the composition. Antioxidant additives such as butylated hydroxyanisole, butylated hydroxyl toluene, tertiary butylhydroquinone, vitamins A, C and E and derivatives, and various plant extracts such as those containing carotenoids, tocopherols or flavonoids having antioxidant properties, may be included to increase the shelf-life of the aromatized carrier. Aroma precursors that would not react during storage but would react to generate aroma during food preparation may also be included in the aromatizing composition.

The production of dehydrated food compositions often involves processing conditions such as elevated temperature, which often causes loss of desirable food aroma. One known technique of overcoming such loss is to add additional aroma and flavour to dehydrated foodstuffs and beverages. Such aromas and flavours are usually complex, comprising many organoleptically active compounds, which combine to create the characterizing aroma of the product. Since aromas and flavours are often extremely powerful and unstable in their undiluted state, they are combined with a carrier to render them more stable and easier to handle. The carriers are preferably neutral or complementary in organoleptic impact and do not contribute to the characterizing aroma of the product. Desirable characteristics of carriers for liquid systems include blandness and miscibility with other liquid carriers and with liquid aromas. Traditional carriers include ethanol, propylene glycol, glycerol, vegetable oil, benzyl alcohol, triacetin, tripropionin, triethyl citrate, and tributyrin.

The aroma constituent of an aromatizing composition characterizes its aroma, i.e., the innate quality that gives the aroma its special attributes among and over other aromas. The aroma constituent may, and often does, include a plurality of aroma ingredients which together result in the characterizing aroma. When a preparation aroma is desired upon rehydration of such flavours and aromas in a dehydrated food or beverage, such compositions are limited in effectiveness because of poor aroma release. When a solid carrier is used, the release of aroma is poor because the diffusion of rehydrating liquid into the particle during rehydration inhibits the counter-diffusion of aroma out. In this way the vast majority of the characterizing aroma constituents end up in the rehydrating liquid. An aroma burst can be obtained by increasing the loading of characterizing aroma constituents into the carrier but this typically leads to an overwhelmingly strong or unbalanced flavour in the product when consumed.

Likewise, poor aroma release is obtained when traditional liquid carriers are used, whether or not they are encapsulated. Those which are water-soluble, suffer the same problems as with soluble solid carriers. The flux of water into the carrier inhibits the diffusion of the aromas out. Furthermore many carriers have a density greater than 1.0 g/cc so they sink in the product during hydration and aromas are released into the rehydrating liquid rather than being released at the surface to effect preparation aroma. Finally, those conventional carriers which do float and are insoluble in water are of an oily or fatty nature. Though these can be arranged to release aroma at the surface they leave an unsightly and often organoleptically and visually undesirable "slick" at the surface of the product.

Natural essential oils from botanical sources are typically intensely flavoured and naturally aromatic due to their inherent volatility. This makes them an ideal choice as aromatizing constituents for use in the manufacture of food products. Unfortunately, volatile essential oils do not exist in all food sources used to manufacture food products. In addition, essential oils that do occur naturally in some foods are often not sufficiently abundant or readily extracted to permit their economical use in processed foods, and some are not approved for food use. Furthermore, many processed foods, due to their intended use, are not able to be manufactured with natural food ingredients that may contain essential oils.

Instant beverage powders typically must quickly and completely dissolve in water without producing insoluble floating or suspended matter or sediment in order to be acceptable to the consumer, and foods or ingredients derived from foods that do contain naturally occurring volatile oils are often not completely water soluble. In response to these limitations, natural or synthetic flavouring agents are typically used to impart the desired character and identity to such food products. In many cases, especially when economically flavoured, the flavouring agent may contain a natural essential oil, such as encapsulated orange oil powders which are used to flavour imitation or orange-flavoured instant beverages. Orange oil is readily and economically pressed from discarded orange peels.

The present invention provides good food preparation aroma without necessarily requiring the use of natural essential oils or the use of amounts of other ingredients, such as vegetable oils, that would adversely affect the properties of foods.

The porosity of the material may be such that the material floats on the surface of the beverage thereby releasing the aroma in the desired "above-cup" location. HF etched mesoporous silicon is also useful in this respect—not only can it be made highly porous and micron sized but it may also be hydrophobic. The high temperature (e.g. 70-100° C.) of the beverages provide so-called burst release of volatile aromas previously entrapped at room temperature within the mesopores by thermal degradation of the capping layer. The mesoporous carrier structure need not be water soluble on the timescales needed for aroma release and hence does not need to be fully porous.

The use of mesoporous materials according to the present invention provides one or more of the following attributes: tunable density to ensure aroma released from floating not submerged particles; non-oily nature thereby avoiding undesirable "slick" on drink surface; hydrophobicity and nanoscale porosity.

Enzymes

Suitable enzymes are selected from the classes of carbohydrases, pectic enzymes, celluloses, proteases, oxidases, and lipases. Examples include amylase, bromelain, catalase, ficin, glucoamylase, glucose isomerase, glucose oxidase, invertase, lactase, lipase, papain, pepsin, pullulanase and rennet.

Prebiotics

A prebiotic is a natural or synthetic substance that supports the growth of and/or nurtures probiotics. More specifically the prebiotic is a nondigestible food ingredient that beneficially affects the host by selectively stimulating the growth and/or activity of one or a limited number of bacteria in the colon. They are typically carbohydrates of relatively short length. Examples are the inulin-type fructans such as lactulose and inulin.

Nutraceuticals

A nutraceutical ingredient provides medical or health benefits, including the prevention and treatment of disease. In general, a nutraceutical is specifically adapted to confer a particular health benefit on the consumer. Suitable nutraceuticals for use in the present invention may be selected from Aloe Vera (*Aloe ferox, A. barbadensis*), Artichoke, Asian Ginseng (*Panax ginseng*), Astragalus, Bee Pollen, Bilberry (*Vaccinium myrtillus*), Black Cohosh, Capsicum-Cayenne, Hot Pepper (*Capsicum* species), Cascara Sagrada (*Rhamnus purshiana*), Cat's Claw (*Uncaria tomentosa*), Chamomile (*Matricaria recutita*), Cranberry, Dandelion (*Taraxacum officinale*), Donq Quai (*Angelica sinensis*), Echinacea (*Echinacea purpurea* and related species), Evening Primrose Oil (*Oenothera biennis*), Feverfew (*Tanacetum parthenium*), Fructo-oligosaccharides, Garlic (*Allium sativum*), Ginger (*Zingiber officinale*), Ginkgo (*Ginkgo biloba*), Ginseng, Glucarate, Glucosamine, Goldenseal (*Hydrastis canadensis*), Gotu Kola (*Centella Asiatica*), Grape Seed Extract, Green Tea, Guarana (*Paullinacupana*), Hawthorne (*Crataegus oxyacantha*), Inositol, Inulin, Isoflavones, Kava Kava (*Piper methysticum*), L-carnitine, Lecithin, Licorice (*Glycyrrhiza glabra* and *G. uralensis*), Lycopene, Milk Thistle (*Silybum marianum*), Mod. Citrus Peel, Nettles, Oligofructose, Omega-3s, Passiflora, Passion Flower (*Passiflora incarnata*), Pau d'Arco, (*Tabebuia impetiginosa*), Peppermint (*Mentha piperita*), Phospholipids, Polyphenol, Psyllium (*Plantago ovata* and *P. Major*), Pycnogenol, Queroetin D-llmonene, Reishi, Ribonucleic Acid, Royal Jelly, St. John's Wort (*Hypericum perforatum*), Saw Palmetto (*Serenoa repens; Sabal serrulata*), Schisandra, Soybean Isoflavones, Tumeric Valerian (*Valeriana officinalis*) and mixtures thereof.

Amino Acids

Suitable amino acids may be selected from Alanine, Arginine, Aspartic Acid, Asparagine, Carnitine, Cysteine, Cystine, Glutamic Acid, Glutamine, Glutathione, Glycine, Histidine, Isoleucine, Leucine, Lysine, Methionine, Ornithine, Phenylalanine, Proline, Serine, Taurine, Threonine, Tryptophan, Tyrosine, Valine and mixtures thereof.

Plant Extracts and Herbs

Suitable plant extracts include one or more plant sterols, these include beta-sitosterol, campesterol, stigmasterol. Suitable plant stanols include sitostanol, octacosanol, policosanol.

Suitable herbs include black walnut, burdock, chamomile, comfrey, Echinacea, eucalyptus, hawthorn, hyssop, ginkgo, hyssop, lemon balm, milk thistle, mullein, peppermint, psyllium, sage, saw palmetto, sheep sorrel, slippery elm, St John's Wort, thyme, turkey rhubarb, valerian, vitex.

Herbs suitable for use for medicinal purposes are described in The Natural Pharmacy by M. Polunin & C. Robbins (Dorling Kindersley 1999), 144 pp. In particular, pages 30-131 list suitable herbs. Suitable culinary herbs are described in Food Commodities, 2nd Edition pp 158-163 by B. Davis (Butterworth Heinemann 1994).

Edible Acids

Suitable edible acids for use in the present invention may be selected from citric acid, ascorbic acid, malonic acid, acetic acid, tartaric acid, sorbic acid, fumaric acid, malic acid, phosphoric acid, succinic acid and nicotinic acid.

Antioxidants

Suitable antioxidants for use in the present invention may be selected from sodium carbonate, calcium carbonate, butylated hydroxyanisole (BHA), butylated hydroxytoluene (BHT), lecithins, sodium lactate, calcium lactate, calcium malate and ammonium citrate.

Food Preparation

Methods for incorporating the mesoporous material into food are numerous. Suitable mixing equipment for use in the present invention is diverse and includes, for example, screw mixers, ribbon mixers and pan mixers. Other examples include high speed propeller or paddle mixers for liquid food or beverages; tumble mixers for dry powders; Z-blade mixers for doughs and pastes. Suitable grinding machines include hammer, disc, pin and ball millers. Extrusion is an important very high throughput (about 300-9000 kg/hr) technique for mixing and providing shape to foodstuffs and is suitable for use in the present invention. Cold and hot extruders may be used. These can be single or twin screw. Extruded foods include cereals, pasta, sausages, sugar or protein based products.

The loading levels can be determined by dividing the volume of the ingredient taken up during loading (equivalent to the mass of the ingredient taken up divided by its density) by the void volume of the mesoporous material (e.g. silicon) prior to loading multiplied by one hundred.

The total quantity of mesoporous material present in the food, based on the weight of the composition according to the present invention, may be about 0.01 to 50 wt %, for example about 0.01 to 20 wt % and for example about 0.1 to 5 wt %.

Embodiments of food compositions according to the present invention include: chocolate formulations comprising mesoporous silicon microparticles of $d_{50}$=20 μm loaded with a bulking agent and/or intense sweetener coated with a 5-10 μm layer of cocoa butter; cereal bars comprising mesoporous silicon microparticles of $d_{50}$=60 μm loaded with lycopene, and coated with an alginate layer of 5-10 μm thickness.

(2) Oral Hygiene Compositions

The mesoporous material may be used in an oral hygiene composition such as a mouthwash or a dentifrice composition such as a toothpaste, tooth powder, lozenge, or oral gel. It may be present as an abrasive in addition to delivering one or more ingredients. The dentifrice composition will comprise constituents well known to one of ordinary skill; these may broadly be characterised as active and inactive agents. Active agents include anticaries agents such as fluoride, antibacterial agents, desensitising agents, antitartar agents (or anticalculus agents) and whitening agents. Inactive ingredients are generally taken to include water (to enable the formation of a water phase), detergents, surfactants or foaming agents, thickening or gelling agents, binding agents, efficacy enhancing agents, humectants to retain moisture, flavouring, sweetening and colouring agents, preservatives and, optionally further abrasives for cleaning and polishing. The oral gel may be of the type suitable for use in multi-stage whitening systems.

Suitable mesoporous microparticulate materials for use in toothpaste include silicon and silica.

Water Phase

The dentifrice composition typically comprises a waterphase which comprises an humectant. Water may be present in an amount of from about 1 to about 90 wt %, preferably from about 10 to about 60 wt %. Preferably, the water is deionised and free of organic impurities. Any of the known humectants for use in dentifrice compositions may be used. Suitable examples include sorbitol, glycerin, xylitol, propylene glycol. The humectant is typically present in an amount of about 5 to 85 wt % of the dentifrice composition.

Anticaries Agent

The dentifrice composition according to the present invention may comprise an anticaries agent, such as a source of fluoride ions. The source of fluoride ions should be sufficient to supply about 25 ppm to 5000 ppm of fluoride ions, for example about 525 to 1450 ppm. Suitable examples of anticaries agents include one or more inorganic salts such as soluble alkali metal salts including sodium fluoride, potassium fluoride, ammonium fluorosilicate, sodium fluorosilicate, sodium monofluorophosphate, and tin fluorides such as stannous fluoride.

Antitartar Agents

Any of the known antitartar agents may be used in the dentifrice compositions according to the present invention. Suitable examples of antitartar agents include pyrophosphate salts, such as dialkali or tetraalkali metal pyrophosphate salts, long chain polyphosphates such as sodium hexametaphosphate and cyclic phosphates such as sodium trimetaphosphate. These antitartar agents are included in the dentifrice composition at a concentration of about 1 to about 5 wt %.

Antibacterial Agents

Any of the known antibacterial agents may be used in the compositions of the present invention. For example, these include non-cationic antibacterial agents such as halogenated diphenyl ethers, a preferred example being triclosan (2,4,4'-trichloro-2'-hydroxydiphenyl ether). The antibacterial agent(s) may be present in an amount of about 0.01 to 1.0 wt % of the dentifrice composition, for example about 0.3 wt %.

Other Abrasive Agents

The mesoporous material can be used as the sole abrasive in preparing the dentifrice composition according to the present invention or in combination with other known dentifrice abrasives or polishing agents. Commercially available abrasives may be used in combination with the mesoporous material and include silica, aluminium silicate, calcined alumina, sodium metaphosphate, potassium metaphosphate, calcium carbonate, calcium phosphates such as tricalcium phosphate and dehydrated dicalcium phosphate, aluminium silicate, bentonite or other siliceous materials, or combinations thereof.

Flavours

The dentifrice composition of the present invention may also contain a flavouring agent. Suitable examples include essential oils such as spearmint, peppermint, wintergreen, sassafras, clove, sage, eucalyptus, majoram, cinnamon, lemon, lime, grapefruit, and orange. Other examples include flavouring aldehydes, esters and alcohols. Further examples include menthol, carvone, and anethole.

Thickening Agents

The thickening agent may be present in the dentifrice composition in amounts of about 0.1 to about 10% by weight, preferably about 0.5 to about 4% by weight. Thickeners used in the compositions of the present invention include natural and synthetic gums and colloids, examples of which include xanthan gum, carrageenan, sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Suitable thickeners also include inorganic thickeners such as amorphous silica compounds including colloidal silica compounds.

Surfactants

Surfactants may be used in the compositions of the present invention to achieve increased prophylactic action and render the dentifrice compositions more cosmetically acceptable. The surfactant is typically present in the dentifrice compositions according to the present invention in an amount of about 0.1 to about 5 wt %, preferably about 0.5 to about 2 wt %. The dentifrice compositions according to the present invention may comprise one or more surfactants, which may be selected from anionic, non-ionic, amphoteric and zwitterionic surfactants. The surfactant is preferably a detersive material, which imparts to the composition detersive and foaming properties. Suitable examples of surfactants are well known to an ordinary skilled person and include water-soluble salts of higher fatty acid monoglyceride monosulfates, such as the sodium salt of the monosulfated monoglyceride of hydgrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals. Further examples include N-lauroyl sarcosine, and the sodium, potassium, and ethanolamine salts of N-lauroyl, N-myristoyl, or N-palmitoyl sarcosine.

Efficacy Enhancing Agents

One or more efficacy enhancing agents for any antibacterial, antitartar or other active agent within the dentifrice composition may also be included in the dentifrice composition. Suitable examples of efficacy enhancing agents include synthetic anionic polycarboxylates. Such anionic polycarboxylates may be employed in the form of their free acids or partially, or more preferably, fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000.

When present, the efficacy enhancing agent, for example the anionic polycarboxylate, is used in amounts effective to achieve the desired enhancement of the efficacy of any antibacterial, antitartar or other active agent within the dentifrice composition. Generally, the anionic polycarboxylate(s) are present within the dentifrice composition from about 0.05 wt % to about 4 wt %, preferably from about 0.5 wt % to about 2.5 wt %.

Other Ingredients

Various other materials may be incorporated in the dentifrice compositions of this invention, including: preservatives; silicones; desensitizers, such as potassium nitrate; whitening agents, such as hydrogen peroxide, calcium peroxide and urea peroxide; and chlorophyll compounds. Some toothpastes include bicarbonate in order to reduce the acidity of dental plaque. These additives, when present, are incorporated in the dentifrice composition in amounts which do not substantially adversely affect the desired properties and characteristics.

Preparation of the Dentifrice Composition

Suitable methods for making the dentifrice compositions according to the present invention include the use of high shear mixing systems under vacuum. In general, the preparation of dentifrices is well known in the art. U.S. Pat. No. 3,980,767, U.S. Pat. No. 3,996,863, U.S. Pat. No. 4,358,437, and U.S. Pat. No. 4,328,205, the contents of which are hereby incorporated by reference in their entirety, describe suitable methods for making dentifrice compositions.

For example, in order to prepare a typical dentifrice composition according to the present invention, an humectant may be dispersed in water in a conventional mixer under agitation. Organic thickeners are combined with the dispersion of humectant along with: any efficacy enhancing agents; any salts, including anticaries agents such as sodium fluoride; and any sweeteners. The resultant mixture is agitated until a homogeneous gel phase is formed. One or more pigments such as titanium dioxide may be combined with the gel phase along with any acid or base required to adjust the pH. These ingredients are mixed until an homogenous phase is obtained. The mixture is then transferred to a high speed/vacuum mixer, wherein further thickener and surfactant ingredients may be combined with the mixture. Any abrasives may be combined with the mixture to be used in the composition. Any water insoluble antibacterial agents, such as triclosan, may be solubilized in the flavour oils to be included in the dentifrice composition and the resulting solution is combined along with the surfactants with the mixture, which is then mixed at high speed for about 5 to 30 minutes, under vacuum of from about 20 to 50 mm of Hg. The resultant product is typically an homogeneous, semi-solid, extrudable paste or gel product.

The pH of the dentifrice composition is typically such that the mesoporous material will not dissolve in the composition over a significant period of time and will thus afford an acceptable shelf-life. The pH of the dentifrice composition is typically less than or equal to about 9 and preferably, particularly for compositions other than powders such as toothpastes, less than or equal to about 7. The lower limit of pH may typically be about 3.5 or about 4. In particular, the pH may be about 3.5 or about 4 when the dentifrice composition is a gel, such as those used in multi-stage whitening systems.

The abrasivity of the dentifrice compositions of the present invention, containing the can be determined by means of Radioactive Dentine Abrasion (RDA) values as determined according to the method recommended by the American Dental Association, as described by Hefferren, J. Dental Research, vol. 55 (4), pp 563-573, (1976) and described in U.S. Pat. No. 4,340,583, U.S. Pat. No. 4,420,312 and U.S. Pat. No. 4,421,527, the contents of which are contained herein by reference in their entirety. In this procedure, extracted human teeth are irradiated with a neutron flux and subjected to a standard brushing regime. The radioactive phosphorus 32 removed from the dentin in the roots is used as the index of the abrasion of the dentifrice tested. A reference slurry containing 10 g of calcium pyrophosphate in 15 ml of a 0.5% aqueous solution of sodium carboxymethyl cellulose is also measured and the RDA of this mixture is arbitrarily taken as 100. The dentifrice composition to be tested is prepared as a suspension at the same concentration as the pyrophosphate and submitted to the same brushing regime. The RDA of the dentifrice compositions according to the present invention may lie in the range of about 10 to 150, for example less than about 100, for example, less than about 70.

The pellicle cleaning ratio (PCR) of the dentifrice compositions of the present invention is a measurement of the cleaning characteristics of dentifrices and generally may range from about 20 to 150 and is preferably greater than about 50.

The PCR cleaning values can be determined by a test described by Stookey et al., J. Dental Research, vol. 61 (11), pp 1236-9, (1982). Cleaning is assessed in vitro by staining 10 mm$^2$ bovine enamel specimens embedded in resin, which are acid etched to expedite stain accumulation and adherence. The staining is achieved with a broth prepared from tea, coffee and finely ground gastric mucin dissolved into a sterilized trypticase soy broth containing a 24-hour Sarcina lutea turtox culture. After staining, the specimens are mounted on a V-8 cross-brushing machine equipped with soft nylon toothbrushes adjusted to 150 g tension on the enamel surface. The specimens are then brushed with the dentifrice composition to be tested and a calcium pyrophosphate standard which comprises 10 g of calcium pyrophosphate in 50 ml of 0.5% aqueous solution of sodium carboxymethyl cellulose. The specimens are brushed with dentifrice slurries consisting of 25 g of toothpaste in 40 g of deionized water, for 400 strokes. The specimens are cleaned with Pennwalt pumice flour until the stain is removed. Reflectance measurements are taken using a Minolta Colorimeter using the standard Commission Internationale de l'Eclairage (CIE) L*a*b* scale in order to measure the colour of the specimens before and after brushing.

The cleaning efficiency of the dentifrice compositions according to the present invention, which is a measure of the ratio of PCR/RDA, may lie in the range from about 0.5 to about 2.0, and may be greater than about 1.0 for example greater than about 1.5.

The use of the mesoporous microparticulate material in an oral hygiene composition may provide one or more of: improved bioavailability of actives and/or increased activity (e.g. of antimicrobial activity). Such improvements may also be achieved at high temperatures, for example, up to about 45° C. over significant periods of time, e.g. for at least 3 months.

An embodiment of a toothpaste formulation according to the present invention comprises mesoporous silicon microparticles of $d_{50}$=30 μm loaded with the hydrophobic antimicrobial triclosan and coated with a 1-5 μm thick layer of starch.

(3) Hair Care Compositions

The term hair care composition as used herein includes shampoos, gels, creams, conditioners (including leave-on conditioners), combined shampoo/conditioners, hair dyes, mousses, foams, waxes, creme rinses, masks, muds, semi-solid structured styling pastes (also known as putties), styling sprays, hot oil treatments, rinses, lotions, all suitable for use on the hair of humans and animals, particularly on human hair, especially hair on the human head. The general constituents of these compositions are well known to the skilled person.

The pH of the hair care composition is advantageously such that the silicon does not dissolve in the composition over a significant period of time and will thus afford an acceptable shelf-life. The pH of the hair care composition is typically less than about 7.5 (though may be as high as about 8.5) and preferably less than or equal to about 7, for example less than or equal to about 6 and may be less than about 4.6. Most commercially available shampoos are, for example, about pH 5-6.5 and the pH of the hair care composition may lie in this range. The lower limit of pH may be about 2. For mesoporous silicon, a suitable pH range may be 2 to 6. For use in higher pH environments, such as up to about pH 8.5 the mesoporous silicon may advantageously be stabilised, for example, by partial oxidation. This may be achieved by heating the mesoporous silicon to about 500° C. over 1 hour in air or an oxygen-rich atmosphere.

Shampoos typically comprise water, surfactant, plus a host of optional further constituents. Water may be present in an amount of about 25% to about 99 wt %, for example about 50% to about 98 wt % based on the weight of the total composition.

Shampoo formulations typically contain high concentrations of surfactants, e.g. up to about 50 wt % based on the total weight of the shampoo. Surfactants may provide a number of functions. For example, they make the removal of dirt easier by reducing the surface tension between the water and the greasy matter on the hair. Any foam produced by the surfactant may hold the dirt in it, and prevent it from being re-deposited on the hair. Surfactants may stabilise the shampoo mixture, and help retain the other ingredients in solution. They may also thicken the shampoo and make it easier to use. Shampoos may contain several surfactants which may provide different types of cleaning, according to the type of hair. One commonly used surfactant is ammonium lauryl sulphate, another is ammonium laureth sulphate, which is milder. Many of the ingredients in shampoos are traditionally soft organic materials.

Most modern shampoos may contain conditioning agent. Other typical ingredients include lather boosters, viscosity modifiers and additives for controlling the pH. The pH of commercially available shampoos may vary quite widely, for example, some shampoos are formulated to be acidic, e.g. about pH 3.5-4.5. Other ingredients may include preservative such as sodium benzoate or parabens. Aesthetic ingredients include colours, perfumes, pearlescing agents.

The hair care compositions according to the present invention may comprise one or more surfactants. The surfactant may be selected from any of a wide variety of anionic, amphoteric, zwitterionic and non-ionic surfactants. The surfactant may be detersive. The amount of surfactant in, for example, the shampoo composition may be from 1 to 50 wt %, for example from 3 to 30 wt %, for example from 5% to 20 wt % based on the total weight of the composition.

Suitable anionic surfactants include alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, alpha-olefin sulphonates and acyl methyl taurates, for example, their sodium, magnesium ammonium and mono-, di- and triethanolamine salts. The alkyl and acyl groups may contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and may contain 2 to 3 ethylene oxide units per molecule.

Particular examples of suitable anionic surfactants include sodium lauryl sulphate, sodium lauryl ether sulphate, ammonium lauryl sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauroyl isethionate, sodium N-lauryl sarcosinate, and mixtures thereof.

Examples of anionic detersive surfactants which may provide cleaning and lather performance to the composition include sulfates, sulfonates, sarcosinates and sarcosine derivatives.

The hair care composition may also include co-surfactants, to help impart aesthetic, physical or cleansing properties to the composition. Suitable examples include amphoteric, zwitterionic and/or non-ionic surfactants, which can be included in an amount ranging up to about 10 wt % based on the total weight of the shampoo composition. Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and lauryl betaine, cocamidopropyl betaine, sodium cocamphopropionate, and mixtures thereof.

Suitable non-ionic surfactants include condensation products of aliphatic ($C_8$ to $C_{18}$) primary or secondary linear or branched chain alcohols or phenols with alkylene oxides, usually ethylene oxide and generally having from 6 to 30 ethylene oxide groups. Other suitable non-ionic surfactants include mono- or di-alkyl alkanolamides. Examples include coco mono- or di-ethanolamide and coco mono-isopropanolamide. Further non-ionic surfactants which can be included in shampoo compositions of the invention are the alkyl polyglycosides (APGs).

Further surfactant may also be present as emulsifier for emulsified components of the composition, e.g. emulsified particles of silicone. This may be the same surfactant as the anionic surfactant or the co-surfactant, or may be different. Suitable emulsifying surfactants are well known in the art and include anionic and non-ionic surfactants. Examples of anionic surfactants used as emulsifiers for materials such as silicone particles are alkylarylsulphonates, e.g., sodium dodecylbenzene sulphonate, alkyl sulphates e.g., sodium lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of non-ionic surfactants used as emulsifiers for materials such as silicone particles are alkylphenol ethoxylates, e.g., nonylphenol ethoxylate nEO, where n is from 1 to 50, alcohol ethoxylates, ester ethoxylates, e.g., polyoxyethylene monostearate where the number of oxyethylene units is from 1 to 30.

The hair care composition may also include one or more conditioning agents. As used herein, the term "conditioning agent" includes any material which is used to give a particular conditioning benefit to hair and/or the scalp or skin. For example, in shampoo compositions for use in washing hair, suitable materials are those which deliver one or more benefits relating to shine, softness, combability, wet-handling, anti-static properties, protection against damage, body, volume, stylability and manageability.

Conditioning agents for use in the present invention include emulsified silicones, used to impart, for example, wet and dry conditioning benefits to hair such as softness, smooth feel and ease of combability. The conditioning agent may be present in a level of from about 0.01 wt % to about 25 wt %, for example about 0.05 to about 10 wt %, for example about 0.1 to 5 wt % based on the total weight of the composition. The lower limit may be determined by the minimum level to achieve conditioning and the upper limit by the maximum level to avoid making the hair and/or skin unacceptably greasy. About 1 wt % is typically suitable.

A further class of silicones for inclusion in shampoos and conditioners of the invention are amino functional silicones. By "amino functional silicone" is meant a silicone containing at least one primary, secondary or tertiary amine group, or a quaternary ammonium group.

A further class of conditioning agents are peralkyl and peralkenyl hydrocarbon materials, used to enhance the body, volume and stylability of hair. Suitable materials include polyisobutylene materials available from Presperse, Inc. The amount of per-alkyl or peralkenyl hydrocarbon material incorporated into the compositions of the invention may depend on the level of body and volume enhancement desired and the specific material used. A suitable amount is from 0.01 to about 10 wt % by weight of the total composition. The lower limit is determined by the minimum level to achieve the body and volume enhancing effect and the upper limit by the maximum level to avoid making the hair unacceptably stiff. An amount of per-alk(en)yl hydrocarbon material of from 0.5 to 2 wt % of the total composition is a suitable level.

A cationic deposition polymer is an ingredient which may be included in shampoo compositions of the invention, for enhancing conditioning performance of the shampoo. By "deposition polymer" is meant an agent which enhances deposition of active ingredients and/or conditioning components (such as silicones) from the shampoo composition onto the intended site during use, i.e. the hair and/or the scalp.

The deposition polymer may be a homopolymer or be formed from two or more types of monomers. The molecular weight of the polymer may typically be at least 10,000, for example, in the range 100,000 to about 2,000,000. The polymers will have cationic nitrogen containing groups such as quaternary ammonium or protonated amino groups, or a mixture thereof. The cationic amines can be primary, secondary or tertiary amines.

As further optional components for inclusion in the hair care compositions of the invention one or more of the following may be included: pH adjusting agents, viscosity modifiers, pearlescers, opacifiers, suspending agents, preservatives, colouring agents, dyes, proteins, herb and plant extracts, and other moisturising and/or conditioning agents.

Any viscosity modifier suitable for use in hair care compositions may be used herein. Generally, the viscosity modifier may comprise from about 0.01 to 10 wt %, for example 0.05 wt % to about 5 wt %, e.g. about 0.1 to 3 wt % based on the weight of the total composition. A non-limiting list of suitable viscosity modifiers can be found in the CTFA International Cosmetic Ingredient Dictionary and Handbook, $7^{th}$ edition, edited by Wenninger and McEwen (The Cosmetic, Toiletry and Fragrance Association, Inc., Washington D.C., 1997).

A wide variety of additional ingredients can be formulated into the hair care compositions according to the present invention. These include: other hair conditioning ingredients such as panthenol, panthethine, pantotheine, panthenyl ethyl ether, and combinations thereof; other solvents such as hexylene glycol; hair-hold polymers such as those described in WO-A-94/08557; viscosity modifiers and suspending agents such as xanthan gum, guar gum, hydroxyethyl cellulose, triethanolamine, methyl cellulose, starch and starch derivatives; viscosity modifiers such as methanolamides of long chain fatty acids such as cocomonoethanol amide; crystalline suspending agents; pearlescent aids such as ethylene glycol distearate; opacifiers such as polystyrene; preservatives such as phenoxyethanol, benzyl alcohol, methyl paraben, propyl paraben, imidazolidinyl urea and the hydantoins; polyvinyl alcohol; ethyl alcohol; pH adjusting agents, such as lactic acid, citric acid, sodium citrate, succinic acid, phosphoric acid, sodium hydroxide, sodium carbonate; salts, in general, such as potassium acetate and sodium chloride; colouring agents; hair oxidising (bleaching) agents, such as hydrogen peroxide, perborate and persulfate salts; hair reducing agents, such as the thioglycolates; perfumes; sequestering agents, such as disodium ethylenediamine tetra-acetate; antioxidants/ultra-violet filtering agents such as octylmethoxycinnamate, benzophenone-3 and DL-alpha tocopherol acetate and polymer plasticizing agents, such as glycerine, diisobutyl adipate, butyl stearate, and propylene glycol. Such optional ingredients generally are used individually at levels from about 0.001 wt % to about 10.0 wt %, preferably from about 0.05 wt % to about 5.0 wt % by weight of the composition.

Mousses, foams and sprays can be formulated with propellants such as propane, butane, pentane, dimethylether, hydrofluorocarbon, $CO_2$, $N_2O$, nitrogen or without specifically added propellants (using air as the propellant in a pump spray or pump foamer package).

Ingredients

The mesoporous material (e.g. silicon) may be loaded with one or more active ingredients. These ingredients include one or more of the following: an anti-dandruff agent or agents, a natural hair root nutrient or nutrients, sunscreen or sunscreens, hair fibre agent or agents, fragrance or fragrances, moisturiser or moisturisers, oil or oils, hair-loss ingredient or ingredients, vitamin or vitamins, head lice agent or agents, structural agent or agents, natural active or actives. Typically, the one or more ingredients are present in the range, in relation to the loaded material (e.g. silicon), of 0.01 to 90 wt %, for example 1 to 40 wt %, for example 20 to 50 wt % (optionally, in combination with about 70% porosity) and for example 2 to 10 wt %.

The ingredient to be loaded with the mesoporous material (e.g. silicon) may be dissolved or suspended in a suitable solvent, and mesoporous material (e.g. silicon) particles may be incubated in the resulting solution for a suitable period of time. Both aqueous and non-aqueous slips have been produced from ground silicon powder and the processing and properties of silicon suspensions have been studied and reported by Sacks in Ceram. Eng. Sci. Proc., 6, 1985, pp 1109-1123 and Kerkar in J. Am. Chem. Soc. 73, 1990, pp 2879-85. The wetting of solvent will result in the ingredient penetrating into the pores of the silicon by capillary action, and, following solvent removal, the ingredient will be present in the pores. Preferred solvents are water, ethanol, and isopropyl alcohol, GRAS solvents and volatile liquids amenable to freeze drying.

In general, if the ingredient to be loaded has a low melting point and a decomposition temperature significantly higher than that melting point, then an efficient way of loading the ingredient is to melt the ingredient.

Higher levels of loading, for example, at least about 15 wt % of the loaded ingredient based on the loaded weight of the material (e.g. silicon) may be achieved by performing the impregnation at an elevated temperature. For example, loading may be carried out at a temperature which is at or above the melting point of the ingredient to be loaded. Quantification of gross loading may conveniently be achieved by a number of known analytical methods, including gravimetric, EDX (energy-dispersive analysis by x-rays), Fourier transform infra-red (FTIR), Raman spectroscopy, UV spectrophotometry, titrimetric analysis, HPLC or mass spectrometry. If required, quantification of the uniformity of loading may be achieved by techniques that are capable of spatial resolution such as cross-sectional EDX, Auger depth profiling, micro-Raman and micro-FTIR.

The loading levels can be determined by dividing the volume of the ingredient taken up during loading (equivalent to the mass of the ingredient taken up divided by its density) by the void volume of the mesoporous material (e.g. silicon) prior to loading multiplied by one hundred.

Anti-Dandruff Agents

Suitable examples of anti-dandruff agents include zinc pyrithione, selenium sulphide, tea tree oil, coal tar, sulphur, salicylic acid, 1 hydroxy pyridone. Further examples are the imidazole anti-fungals including miconazole, imidazole, fluconazole, piroctone, clotrimazole, bifonazole, ketaconazole, climbazole, olamine(octopirox), rilopirox, ciclopirox, olamine.

Sunscreens

Suitable sunscreens include camphor derivatives, benzophenone compounds such as 4,4'-tetrahydroxy-benzophenone which is sold commercially as Uvinui D50, and 2-hydroxy-4-methoxybenzophenone, sold commercially as Eusolex 4360, dibenzoyl methane derivatives such as t-butyl-4-methoxydibenzoylmethane, sold commercially as Parsol 1789, and isopropyldibenzoyl methane, sold commercially as Eusolex 8020.

Further suitable types of sunscreen materials are cinnamates, such as 2-ethylhexyl-p-methoxy cinnamate, sold commercially as Parsol MCX, 2-ethoxy ethyl-p-methoxy cinnamate, sold commercially as Giv-Tan F and isoamyl-p-methoxy cinnamate, sold commercially as Neo-Heliopan E1000.

Natural Hair Root Nutrients

Suitable natural hair root nutrients include amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

Hair Fibre Benefit Agents

Suitable examples of hair fibre benefit agents include ceramides, for moisturising the fibre and maintaining cuticle integrity. Ceramides are available including by extraction from natural sources, or as synthetic ceramides.

Other suitable materials include fatty acids, for cuticle repair and damage prevention. Particular examples include branched chain fatty acids such as 18-methyleicosanoic acid and other homologues of this series, straight chain fatty acids such as stearic, myristic. and palmitic acids, and unsaturated fatty acids such as oleic acid, linoleic acid, linolenic acid and arachidonic acid.

Split ends may be treated and/or prevented by using a lubricating or plasticizing agent. The surface chemistry of the mesoporous silicon may be adapted to promote hair binding. For example, the fraction of an active ingredient, such as a hydrophobic active ingredient, that is retained on the hair may be improved by at least 50% when compared to the free active ingredient and/or its dissolution improved upon application to the hair, for example by at least 500%.

Hair-Loss Ingredients

One or more ingredients suitable for the prevention and/or treatment of hair-loss may be included. Suitable hair loss preventive agents include non-steroidal anti-inflammatories such as piroxicam, ketoprofen, ibuprofen, circulation stimulators such as capsicum or gotu kola. Minoxidil or zinc pyridinethione (ZPT), plant extracts such as aloe vera, ginko biloba, olive oil, vitamin E, vitamin B3 and amino acids.

Head Lice Agents

Suitable actives include insecticides and/or pesticides such as pyrethrins, essential oils, malathion compounds, avermectin compounds.

Fragrances

Suitable fragrances, or perfuming ingredients, include compounds belonging to varied chemical groups such as aldehydes, ketones, ethers, nitrites, terpenic hydrocarbons, alcohols, esters, acetals, ketals, nitriles. Natural perfuming agents are preferred such as essential oils, resinoids and resins.

With regard to fragrant oils, sustained release may be carried out using mesoporous silicon possessing a pore diameter in the range of about 1-10 nm. The small pore size suppresses the release of the fragrant volatiles.

Moisturisers

Suitable moisturisers or emollients include glycerine, mineral oil, petrolatum, urea, lactic acid or glycolic acid.

Oils

Suitable oils include plant oils, essential oils.

Vitamins

Suitable vitamins include vitamin A, B5, C, E.

Structural Agents

Suitable structural agents include oils, proteins, polymers that thicken and add body to hair and/or make it feel smoother. Structural agents which add body may be referred to as bulking agents or bulk agent coatings and may be suitable for use with fine hair follicles. These may be colour matched and/or provide a muted glitter appearance with the hair and/or combined with one or more fragrances.

Natural Actives

Suitable natural actives include herb or plant extracts. Light sensitive plant actives are suitable for use in accordance with the present invention. Entrapment within mesoporous silicon and gradual release provides for improved shelf-life and on-hair photostability.

Mixtures of any of the above active ingredients may also be used.

An embodiment of a shampoo formulation according to the present invention comprises mesoporous silicon microparticles of $d_{50}=50$ μm loaded with ketaconazole and coated with a 2-5 μm thick layer of glyceryl oleate.

(4) Cosmetic Formulations

Cosmetic formulations generally refer to substances or preparations intended for placement in contact with an external part of the human body with a view to providing one or more of the following functions: changing its appearance, altering the odour, cleansing, maintaining/improving the condition, perfuming and protecting.

The mesoporous material may comprise at least one ingredient for delivery to the face or body. Suitable ingredients include one or more of: antioxidants, anti-ageing actives, skin lightening agents, nutrients, moisturisers, antimicrobials, fragrances, oils, vitamins, structural agents, natural actives. The mesoporous material may be loaded with the ingredient which may be entrapped in the material pores.

The use of mesoporous material containing cosmetic formulations according to the present invention seeks to provide one or more of the following: targeted delivery of ingredients; extended release of ingredients including burst fragrance release, for example, during washing; sebum absorption/removal; improved bioavailability of actives, including hydrophobic actives; skin exfoliation; beneficial degradation products such as orthosilicic acid; retention of significant levels of active ingredients on the body or face over extended periods of time, excellent skin feel and visual appearance.

Suitable antioxidant agents include pycnogenol, plant and fruit extracts, marine extracts, ascorbic acid, glucosides, vitamin E, herbals extracts and synergistic combinations thereof. Suitable anti ageing actives include ceramide, peptides, plant extracts, marine extracts, collagen, calcium amino acids vitamin A, vitamin C and CoQ10. Suitable skin lightening agents include liquorice, arbutin, vitamin C, kojic acid. Suitable moisturisers include panthenol, amino acids, hyaluronic acids, ceramides, sodium PCS, glycerols and plant extracts.

Cosmetic compositions suitable for use in accordance with the present invention may be in the form of creams, pastes, serums, gels, lotions, oils, milks, stick, ointments, powder (including dry powder), solutions, suspensions, dispersions and emulsions.

Suitable cosmetic compositions include: foundation, mascara, nail laquer, nail enamel, deodorant, lipstick, lip balm, lip gloss, colour cosmetics, face cream, eye cream, toner, cleanser, aftersun, moisturiser, shaving cream, after shave, face masks, lip and eye liners, face powder (loose and pressed), eye shadow, bronzer, blush, concealers, face scrub and make up removers. The components comprised in these compositions are well known to the skilled person and these components are suitable for use in the present invention. These components may include a vehicle to act as a carrier or dispersant, emollients, thickeners, opacifiers, perfumes, colour pigments, skin feel components, other sebum absorbing materials, preservatives, mineral fillers and extenders, colour pigments.

In general, cosmetic compositions may contain a vehicle to act as a carrier or dispersant for the mesoporous material so as to facilitate the distribution of the mesoporous material when the composition is applied to the skin. Vehicles other than, or in addition to water can include cosmetic astringents, liquid or solid emollients, emulsifiers, film formers, humectants, skin protectants, solvents, propellants, skin-conditioning agents, solubilising agents, suspending agents, surfactants, ultraviolet light absorbers, waterproofing agents, viscosity increasing agents, waxes, wetting agents. The carrier or dispersant may form about 50 to 90 wt % of the composition. An oil or oily material may be present to provide a water in oil or oil in water emulsion. The compositions may contain at least one active ingredient including skin colourants, drug substances such as anti-inflammatory agents, antiseptics, antifungals, steroids or antibiotics.

Levels of emollients may be 0.5 wt % to 50 wt %, for example 5 to 30 wt %. General classes of emollients include esters, fatty acids, alcohols, polyols, hydrocarbons. Examples of esters include dibutyl adipate, diethyl sebacate, lauryl palmitate. Suitable alcohols and acids include those having from 10 to 20 carbon atoms, for example cetyl, myristyl, palmitic and stearyl alcohols and acids. Examples of polyols include propylene glycol, sorbitol, glycerine. Suitable hydrocarbons include those possessing 12 to 30 carbon atoms, e.g. mineral oil, petroleum jelly, squalene.

A thickener may be present in levels from 0.1 to 20 wt %, for example about 0.5 to 10 wt %. Examples of suitable thickeners include gums e.g. xanthan, carrageenan, gelatin. Alternatively, the thickening function may be provided by any emollient which is present.

Suitable mineral fillers or extenders include chalk, talc, kaolin mica.

Other minor components may be incorporated into the cosmetic compositions, such as skin feel components. Skin feel components may also include colouring agents, opacifiers and perfumes. These minor components may range from 0.001 wt % to 10 wt %.

Other suitable ingredients may include sebum absorbing materials (other than mesoporous silicon) such as starch, colour pigments, e.g. iron oxides, preservatives such s trisodium EDTA. Other minor components include colouring agents, perfumes, opacifiers which may range from 0.01 to 10 wt %.

Lipstick typically contains pigments, oils, waxes, and emollients that applies colour and texture to the lips. Lip balm is a substance topically applied to the lips of the mouth to relieve chapped or dry lips. Lip gloss is topically applied to the lips of the mouth, but generally has only cosmetic properties. Lip balm may be manufactured from beeswax, petroleum jelly, menthol, camphor, scented oils, and various other ingredients. Other ingredients such as vitamins, alum, salicyclic acid or aspirin may also be present. The primary purpose of lip balm is to provide an occlusive layer on the lip surface to seal moisture in lips and protect them from external exposure. The occlusive materials like waxes and petroleum jelly prevent moisture loss and maintain lip comfort while flavourants, colorants, sunscreens and various medicaments can provide additional, specific benefits. Lip balm usually comes in containers for application with the fingers or in stick form which is applied directly to the lips.

Mascaras can broadly be divided in two groups: water resistant mascaras (often labelled waterproof) and non-water resistant mascaras. Water resistant mascaras have a composition based on a volatile solvent (e.g. isododecane), animal-derived waxes (e.g. beeswax), vegetal based waxes (e.g. carnauba wax, rice bran wax, candelila wax), mineral origin wax (ozokerite, paraffin), pigments (e.g. iron oxide, ultramarine) and film forming polymers. These mascaras do not contain water-sensitive moieties and afford resistance to tears, sweat or rain. Non water-resistant mascaras are based on water, soft surfactants (e.g. triethanolamine stearate), animal-derived waxes (e.g. beeswax), vegetal based waxes (e.g. rice bran wax, candelilla wax), mineral origin waxes (ozokerite, paraffin), pigments (iron oxide, ultramarine), thickening polymers (gum arabic, hydrophobically modified cellulose) and preservatives. These mascaras can run under the effect of tears, but are easily removed with soap and water. Polymers in a water dispersed form (latexes) can bring some level of water resistance to the group of normally non-water resistant mascaras. Waterproof mascaras are similar to oil-based or solvent-based paints. Non water-resistant mascaras behave like water based paints. For intermediate water sensitivity, mascaras contain polymer dispersions.

Face powder is typically applied to the face to set foundation after application. It is absorbent and provides toning to the skin. It can also be reapplied throughout the day to minimize shininess caused by oily skin. There is translucent sheer powder, and there is pigmented powder. Certain types of pigmented facial powders are meant to be worn alone with no base foundation. Powder tones the face and gives an even appearance. Besides toning the face, some SPF based powders can also reduce skin damage from the sun and environmental stress. It comes packaged either as a compact or as loose powder. It can be applied with a sponge, brush, or powder puff. Due to the wide variation among human skin tones, there is a corresponding variety of colours of face powder. There are also several types of powder. A common powder used in beauty products is talc. Some commercially available brands may contain natural mineral ingredients. Such products are promoted as being safe and calming for rosacea, as well as improving wrinkles and skin that has been over exposed to sun and has hyper pigmentation. Powdering is a very popular cosmetic technique and is used by many people.

An embodiment of a cosmetic formulation according to the present invention comprises spheroidized mesoporous silicon microparticles of $d_{50}=10$ μm co-loaded with skin lightening agent (kojic acid), a moisturizing agent (panthenol), and capped with a 300-500 nm layer of paraffin.

EXAMPLES

The invention will now be described by way of example only with reference to the following examples.

Alginate is a salt of alginic acid which is found in brown algae. It is a polysaccharide made of mannuronic and guluronic acid whose carboxyl groups are capable of forming gels in the presence of divalent cations such as calcium and magnesium (ionotropic gelling). The divalent cations are chelated by the carboxylate groups of the polymer. This chelation results in the formation of electrostatic bridges, which stiffen the gel. The ratio between guluronic and mannuronic monomers affects the structural properties of the gel. Chitosan is a linear polysaccharide composed of D-glucosomine and N-acetyl-D-glucosomine.

Example 1

Mesoporous silicon microparticles of mean diameter 10 μm loaded with active material (hydrophilic coloured food dye), are dispersed in a 0.5-4% alginate solution at high concentrations (e.g. 50-80 wt % Si content). The mixture is vortexed at 150-300 rpm for 3-4 hours. The solution is filled in a syringe and a suitable needle (21-26 gauge) is used to drop the mesoporous silicon dispersed alginate solution in a 0.05-0.2M calcium chloride solution. The resultant droplets of alginate form beads instantaneously. The beads can be washed and air-dried to evaporate the water content and each bead will have a few microparticles of mesoporous silicon loaded with active material. The results indicate that coating of mesoporous silicon with alginate resulted in the successful retention of hydrophilic coloured food dye in water compared to controls which were not capped. A modified emulsion based process such as that described in Mofidi et al. Process BioChemistry 35, 885-888 (2000), can be used for significantly higher throughput production.

Example 2

Mesoporous silicon microparticles were fabricated from anodized membranes. The mesoporous membranes were loaded with triclosan by melt-loading and then ground with a pestle and mortar. The samples of mesoporous silicon were: (a) 70 vol % mesoporous silicon loaded with 58.4 wt % triclosan, (b) 71 vol % mesoporous silicon loaded with 57.4 wt % triclosan. The loaded samples of porous silicon were coated with (i) chitosan and (ii) alginate. For the purposes of comparison, triclosan was also loaded into mesoporous silicon (64.2 vol % porosity) which was not subsequently coated and into chitosan and alginate separately. Alginate and chitosan microbeads were prepared using a 5 ml Plastipak syringe possessing a 21 gauge needle.

In order to develop a suitable assay for triclosan, triclosan was dissolved in ethanol at a concentration of 5 mg/ml and in water at 100 μg/ml. The absorption scan of the resulting solutions was run on a UV visible spectrophotometer (Thermo-Fisher spectrophotometer UV10) from 190-500 nm. Peak absorptions were obtained at 280 nm in both solutions. Standard plots of absorbance (nm) versus concentration of triclosan (μg/ml) were obtained of triclosan in ethanol, water and 0.05% sodium dodecyl sulphate (SDS).

Triclosan was loaded in an anodized porous silicon membrane at a loading of 58.4 wt %. It was then ground to a fine powder using a mortar and pestle. 2 ml of 2% alginate solution was added to 10-11 mg of the ground powder (which contained 5-6 mg of loaded triclosan) and the mixture was vortexed vigorously. For the purposes of comparison, 5-6 mg of triclosan were encapsulated in (i) alginate beads only and (ii) mesoporous silicon powder. After washing the prepared samples with deionised water, the various samples were separately suspended in 0.05% SDS to monitor the release of triclosan. The concentration of triclosan was measured spectroscopically at 280 nm.

The results indicated about 8 wt % release of triclosan from the mesoporous silicon sample coated with alginate beads, 16 wt % release from the alginate only sample, 25 wt % release from the mesoporous silicon powder sample, all over a period of 24 hours.

About 2 wt % of chitosan was dissolved in 1M acetic acid at 45° C. An aqueous solution of sodium tri polyphosphate solution was prepared and the pH of the solution was adjusted to 3. The chitosan solution was vortexed with mesoporous silicon powder vigorously to yield a mixture. This mixture/chitosan solution alone yields hydrogel beads if allowed to fall drop wise in acidic sodium tri polyphosphate solution.

Triclosan was loaded in an anodized porous silicon membrane at a loading of 57.4 wt %. It was then ground using a mortar and pestle to a fine powder. 28.7 mg of the loaded ground powder (containing about 16 mg of triclosan at a loading of 57.4 wt %) was mixed with 2 ml of 2% chitosan solution to yield beads. About 11 mg of triclosan encapsulated in chitosan only and 20 mg of triclosan loaded into mesoporous silicon powder were prepared for the purposes of comparison.

Triclosan release from the various formulations was studied by suspending the formulations in 0.05 SDS solution for about 4 days at ambient temperature. At different times, the samples were collected and release of the triclosan determined spectroscopically. Significant reduction of triclosan release was found with chitosan coated porous silicon particles. Over a period of 4 days, the results indicated a 2.7% release of triclosan from chitosan coated porous silicon particles, about 5% release from chitosan and 20% release from mesoporous silicon.

The chemical stability of the capping materials, alginate and chitosan, was assessed gravimetrically. Stability studies were carried out in SDS media of chitosan and alginate hydrogels. 0.45 to 0.58 g of alginate beads and 0.35 to 0.45 g of chitosan beads were suspended in 10 ml of 0.05% SDS media for varying periods of time at 20° C. Over time periods varying from 1 to 5 days, the beads were removed from the media and reweighed to examine for any weight loss. The results indicated that both alginate and chitosan weight loss was <1% in SDS media after 5 days. These results show that both of these polymers are relatively stable indicating their suitability for use in a range of compositions including toothpaste formulations.

Example 3

A mesoporous synthetic carbon was produced from a phenolic resin and a suitable pore former and cross linking agent. The size of the mesopores was about 25 nm, there were also present a small number of micropores of about 0.8 nm. The product was cured and washed and then carbonised and activated as described in US 2008090924, the contents of which hereby incorporated in their entirety by reference. The BET surface area of the sample was 1044 $m^2/g$ and the pore volume was 1.02 cc/g. This spherodized mesoporous carbon (size fraction, i.e. the sieved range of particle diameter, was 250-500 µm) was loaded with ethyl butyrate by adding the oil drop wise into the powder and mixing until the wet point was reached. Excess oil added was allowed to evaporate and the final weight of the free-flowing loaded powder was recorded. A 10% aqueous solution of gum arabic and maltodextrin (70:30 ratio) was used as the encapsulating material. The loaded spherodized carbon was suspended in the polymer blend and spray dried using a BUCHI Mini Spray Dryer B-290 with the following parameters: inlet temperature 130° C., aspirator 100%, pump rate 25%, air flow 831 liters/hour at STP and outlet temperature 75-80° C. The uncapped carbon powder was black in colour; the spray dried powder with entrapped flavour was white.

The invention claimed is:

1. A composition comprising a mesoporous microparticulate silica material, wherein at least some of the pores of the silica are loaded with at least one ingredient and said at least one ingredient is a protein or a peptide and the loaded mesoporous microparticulate silica material is encapsulated by a polymeric capping layer and wherein the capping layer is 0.1 to 50 µm thick, the capping layer is a bead and the bed encapsulates more than a single mesoporous microparticle.

2. A composition according to claim 1, wherein the polymeric capping layer is a biodegradable polymeric capping layer.

3. A composition according to claim 1, wherein the protein is an enzyme.

4. A composition according to claim 1, wherein the capping layer is prepared by spray drying.

5. A composition according to claim 1, wherein the size of the pores is about 10 nm to about 25 nm.

6. A composition according to claim 1, wherein the mesoporous material is biodegradable.

* * * * *